United States Patent [19]

Sheldon et al.

[11] 4,110,360

[45] Aug. 29, 1978

[54] PREPARATION OF ESTERS

[75] Inventors: Roger A. Sheldon; Peter Been, both of Amsterdam, Netherlands; Derek A. Wood, Sittingbourne; Ronald F. Mason, Ashford, both of England

[73] Assignee: Shell Oil Company, Houston, Tex.

[21] Appl. No.: 765,184

[22] Filed: Feb. 3, 1977

[30] Foreign Application Priority Data

Mar. 1, 1976 [GB] United Kingdom ................. 8044/76

[51] Int. Cl.² ................... C07C 120/00; C07C 121/66
[52] U.S. Cl. ............................................... 260/465 D
[58] Field of Search ................................... 260/465 D

[56] References Cited

U.S. PATENT DOCUMENTS 3,835,176  9/1974  Matsuo et al. ................... 260/465 D

OTHER PUBLICATIONS

Zymalkowski et al., Arch. Pharmaz. Ber. Pharmaz. Ges. 62, No. 5, pp. 218–224, (1956).
Francis et al., J. Chem. Soc., 95, pp. 1403–1409, (1909).
Kinder et al., Arch. Pharm., 271, pp. 431–439, (1933).
Coronyn, J. Org. Chem., 14, pp. 1013–1022, (1949).
Fisher et al., J. Org. Chem., 24, pp. 1650–1654, (1959).

*Primary Examiner*—Dolph H. Torrence

[57] ABSTRACT

Certain carboxylic acid esters also containing a cyano group are prepared by reacting an acid halide, an aldehyde and a water-soluble cyanide in the presence of a water immiscible aprotic solvent and preferably a phase-transfer catalyst.

14 Claims, No Drawings

PREPARATION OF ESTERS

BACKGROUND OF THE INVENTION

1. Field of the Invention

The invention relates to a process for the preparation of certain cyano-substituted-carboxylic acid esters by reacting an acid halide, an aldehyde and a water-soluble cyanide.

2. Description of the Prior Art

According to U.S. Pat. No. 3,835,176, addition of substituted cyclopropanecarbonyl halides and m-substituted benzaldehydes, if necessary dissolved in an aprotic solvent, to an aqueous solution of sodium cyanide or potassium cyanide and stirring of the mixture obtained until no more conversion takes place, affords the desired esters. The experiment described in Example 4 of the above U.S. patent was conducted in the absence of a solvent, with an unsaturated aqueous solution of sodium cyanide, with a 20% molar excess of the cyclopropanecarbonyl halide (calculated on aldehyde) and at a temperature of 0° C.

Such a process has the disadvantages that the yield of the ester is relatively low and that keeping the temperature at 0° C and using the said molar excess are expensive.

The present invention obviates these disadvantages.

SUMMARY OF THE INVENTION

The present invention is directed to a process for preparing an ester of the formula I

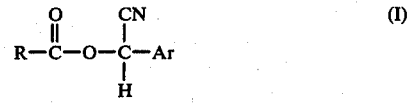

wherein R is an optionally substituted acyclic or saturated cyclic hydrocarbyl group and Ar is an optionally substituted aromatic group by contacting an aromatic aldehyde of the formula

ArCH and an acyl halide of the formula

RCHal in which formulas Ar and R have the same meanings in the formula I and Hal is a halogen atom having an atomic number from 9 to 53, inclusive, in the presence of a substantially water-immiscible aprotic solvent, with water and solid water-soluble cyanide.

It has been found that when in a given case in which in successive comparable experiments less water and more solid water-soluble cyanide are applied (starting from a saturated aqueous solution of cyanide containing no solid water-soluble cyanide and keeping the total amount of water-soluble cyanide constant) the reaction time can be kept shorter and shorter, passes a minimum and then becomes longer and longer until it has become as long as in the starting case.

The most suitable substantially water-immiscible aprotic solvent is a (cyclo)alkane having up to 10 carbon atoms, preferably 6 to 10 carbon atoms, or a mixture of (cyclo)alkanes, because they allow the shortest reaction times. The use of these solvents is covered in our concurrently filed U.S. patent application Ser. No. 765,188. Examples of suitable (cyclo)alkanes are n-hexane, n-heptane, n-octane, n-nonane, n-decane and their isomers (for example 2-methylpentane, 3-methylpentane, 2-methylhexane, 3-methylhexane and 2,4,4-trimethylpentane) and cyclohexane and methylcyclohexane. Gasolines rich in alkanes are also very suitable, for example with boiling range at atmospheric pressure between 40° and 65° C, 60° and 80° C or 80° and 110° C. Very good results have been obtained with n-heptane and cyclohexane. The molar ratio of the amount of water to the total amount of water-soluble cyanide can be kept very low in the presence of alkanes or cycloalkanes as the substantially water-immiscible aprotic solvent, and is suitably higher than 0.005 and preferably higher than 0.01.

Other very suitable substantially water-immiscible aprotic solvents are aromatic hydrocarbons and chlorinated hydrocarbons, for example benzene, toluene, o-, m- and p-xylene, the trimethylbenzenes, dichloromethane, 1,2-dichloroethane, chloroform, monochlorobenzene and 1,2- and 1,3-dichlorobenzene. Very good results have been obtained with toluene. The molar ratio of the amount of water to the total amount of water-soluble cyanide is suitably higher than 0.05 in the presence of aromatic hydrocarbons and chlorinated hydrocarbons.

The above-mentioned minimum reaction time is usually obtained when molar ratios of the amount of water to the total amount of water-soluble cyanide in the range of from 0.05 to 1 are applied in the presence of (cyclo)alkanes, aromatic hydrocarbons and chlorinated hydrocarbons.

For comparison it may be stated that the molar ratios of water to sodium cyanide in a saturated aqueous solution of sodium cyanide at 10° and 35° C are 5.7 and 3.3, respectively. Consequently, extremely small amount of water are sufficient to obtain the shortest reaction time. Furthermore, the yield of the ester of the formula I is usually very high and in many cases quantitative or almost quantitative.

In addition to the possibility of using short reaction times the use of solid water-soluble cyanide has a cost-saving effect, since smaller volumes of water can be handled.

Other examples of substantially water-immiscible aprotic solvents are dialkylethers and substantially water-immiscible alkanones, for example diethyl ether, diisopropyl ether and diisobutyl ketone. For these solvents the above-mentioned minimum reaction time can easily be determined by means of simple experiments in which the molar ratio of the amount of water to the total amount of water-soluble cyanide is varied.

The temperature at which the process is conducted is suitably above 0° C and is preferably in the range of from 10° to 50° C, and particularly 15° to 40° C. The process has as an advantage that ambient temperatures are very suitable.

Mixtures of solvents, for example of alkanes and aromatic hydrocarbons may be applied, for example of n-heptane containing up to 10 %m of benzene and/or toluene.

It has also been found that the presence of a phase transfer catalyst further shortens the reaction time; such a catalyst is particularly useful in the presence of the water-immiscible aprotic solvents which are not (cyclo)alkanes, particularly in the presence of aromatic hydrocarbons and chlorinated hydrocarbons. The phase transfer catalysts may, however, also be used in the presence of alkanes or cycloalkanes, but the reaction times can already be kept very short in the absence of this catalyst. The phase transfer catalyst may be any reagent which is capable of accelerating interphase reactions in aqueous/organic two-phase systems. The use of phase transfer catalysts is covered in our concurrently filed U.S. patent applications Ser. No. 765,186, 765,187 and 765,185.

The phase transfer catalyst may be an onium compound:

(1) a quaternary onium compound of the formula

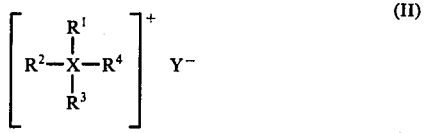
(II)

wherein X is a nitrogen, phosphorus or arsenic atom, $R^1$, $R^2$, $R^3$ and $R^4$ each independently is an alkyl group of 1 to 20 carbon atoms, an aralkyl or alkaryl group of 7 to 9 carbon atoms or an aryl group of 6 to 12 carbon atoms and Y is a monovalent ion; or (2) a sulfonium compound of the formula

(III)

wherein $R^5$, $R^6$ and $R^7$ each independently is an alkyl group of 1 to 40 carbon atoms and Y is a monovalent ion.

In formulas II and III above, Y can be hydroxide, halide, (alkyl)sulfate, (alkyl)sulfonate, (aryl)sulfonate, tetrafluoroborate, phosphate, nitrate or alkyl- or arylcarboxy- (all six trade names are registered trademarks). Very good results have been obtained with those derived from trimethylamine. When these catalysts are available in a neutralized form, for instance in the chloride form, they must be activated to the hydroxyl form by treatment with an aqueous alkali metal hydroxide, for example sodium hydroxide, and washed with water to remove salt anions before use.

More particularly, one preferred subclass of catalysts of formula II are those in which $R^1$, $R^2$, $R^3$ and $R^4$ each independently is an alkyl group of 1 to about 8 carbon atoms such as methyl-trioctylammonium chloride, tributylammonium bromide, tetra-n-butylammonium hydroxide, bromide or chloride, methyl-tri-2-methylheptylammonium chloride, tetramethylammonium bromide, tetrabutylphosphonium bromide or tetraethylammonium bromide. Other suitable catalyst of this type are known under the trade names "Hyamine 1622", "Hyamine 2389", "Hyamine 3500", "Aliquat 336" and "Adogen 464" (all five trade names are registered trademarks).

Another preferred subclass of catalysts of formula II are those containing one or more phenyl or benzyl groups as $R^1$, $R^2$, $R^3$ and $R^4$ such as benzyltriethylammonium chloride or ethyltriphenylphosphonium bromide or the like.

Examples of catalysts of formula III are triethylsulfonium iodide, di-sec-decyl-methylsulfonium chloride, n-hexadecyldimethylsulfonium methyl sulfate, sec-dodecyl-sec-hexadecylethylsulfonium ethyl sulfate, sec-hexadecyldimethylsulfonium iodide, sec-hexadecylmethylethylsulfonium tosylate, sec-hexadecyldimethylsulfonium tosylate, trimethylsulfonium bromide and di-n-butylmethylsulfonium iodide. Preferred catalysts of formula III are those in which $R^5$, $R^6$ and $R^7$ each late. For example, Y can be choride, bromide, iodide, methylsulfate, tosylate, acetate, formate, citrate, tartrate benzoate or the like.

Examples of suitable onium compounds are tetra-n-butylammonium bromide, tetra-n-butylammonium chloride, methyltri-2-methylphenylammonium chloride, tetramethylphosphonium iodide, tetra-n-butylphosphonium bromide, methyltriphenylarsonium iodide, ethyl-2-methylpentadecyl-2-methylundecylsulfonium ethylsulfate, methyldinonylsulfonium methylsulfate and n-hexadecyldimethysulfonium iodide. Further suitable onium compounds are described in U.S. Pat. No. 3,917,667 and allowed U.S. Ser. Nos. 587,783 and 587,574. Very good results have been obtained with quaternary ammonium compounds.

The onium compound may be a hydroxide or salt and is used as the functional portion of a strongly basic anion exchange resin having a structural portion (polymer matrix) and a functional portion (ion-active group). Of special importance are polystyrene resins, such as copolymers of aromatic monovinyl compounds and aromatic polyvinyl compounds, particularly styrene/divinylbenzene copolymers. The functional portion is a quaternary ammonium, phosphonium or arsonium group. Examples of strongly basic anion exchange resins which may be employed are those derived from trimethylamine (such as the products known under the trade names of "Amberlite IRA-400", "Amberlite IRA-401", "Amberlite IRA-402", "Amberlite IRA-900", "Duolite A-101-D", "Duolite ES-111", "Dowex 1", "Dowex 11", "Dowex 21K" and "Ionac A-450" (all ten trade names are registered trade marks) and those derived from dimethylethanolamine (such as the products known under the trade names of "Amberlite IRA-410", "Amberlite IRA-911", "Dowex 2", "Duolite A-102-D", "Ionac A-542" and "Ionax A-550" independently is an alkyl group of 3 to 16 carbon atoms. The preparation of catalysts of formula III is described in U.S. Pat. No. 3,917,667.

Suitable phase transfer catalysts are -hexaoxacyclooctadecane polyethers known as "crown ethers". These compounds, together with their preparation, are described in the literature, for example in Tetrahedron Letters No. 18(1972) pp. 1793–1796, and are commonly designated by reference to the total number of atoms forming the macrocyclic ring together with the number of oxygen atoms in that ring. Thus the macrocyclic polyether whose formal chemical name is 1,4,7,10,13,16-hexaoxacyclooctadecane is designated as "18-crown-6". Other examples of suitable macrocyclic polyethers are 3,4-benzo-1,6,9,12,15,18,21-heptaoxacyclotricos-3-ene and 3,4-benzo-1,6,9,12,-tetraoxacyclotetradec-3-ene. 18-Crown-6 is particularly suitable. Further suitable macrocyclic polyethers and their preparation are described in U.S. Pat. No. 3,562,295, British Pat. No. 1,108,921 and Netherlands publication No. 7,602,604.

Thus, useful macrocyclic polyethers can have from 15 to 30 ring atoms in the polyether ring and consist of from 5 to 10 —O—X— units wherein X for a particular compound is either

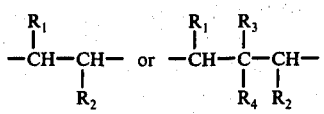

in which $R_1$ $R_2$ $R_3$ and $R_4$ are radicals independently selected from the group consisting of hydrogen and alkyl radicals having from 1 to 4 carbon atoms with the proviso that when the —O—X— units comprise

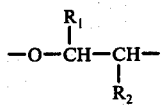

one of X can be (b). For example:
1,4,7,10,13,16-hexaoxacyclooctadecane,
1,4,7,10,13-pentaoxacyclopentadecane,
1,4,7,10,13,16,19-heptaoxacycloheneicosane,
1,4,7,10,13,16,19,22-octacyclotetracosane, and
1,4,7,10,13,16,19,22,25,27-decaoxacyclotriacontane Other, useful macrocyclic polyethers can contain 4 to 80 atoms, preferably 14-28 are ring atoms of which at least 4 and preferably 5 to 8 are oxygen atoms. Up to 10 carbon atoms can be present between one or more pairs of oxygen atoms with at least 1 aromatic nucleus attached to the polyether ring by means of vicinal carbon atoms of the aromatic nucleus. The aromatic nucleus may be optionally substituted by halogen, alkyl, cyano, amino, nitro, hydroxy and carboxy radicals. For example:
2,3-benzo-1,4,7,10-tetraoxacyclododeca-2-ene,
2,3,8,9-dibenzo-1,4,7,10-tetraoxacyclododeca-2,8-diene,
2,3,9,10-dibenzo-1,4,8,11-tetraoxacyclotetradeca-2,9-diene,
2,3,9,10-bis(t-butylbenzo)-1,4,8,11-tetraoxacyclotetradeca-2,9-diene,
2,3,8,9-dibenzo-1,4,7,10,13-pentaoxacyclopentadeca-2,8-diene,
2,3,9,10-dibenzo-1,4,8,11,14-pentaoxacyclohexadeca-2,9-diene,
2,3,11,12-dibenzo-1,4,7,10,13-pentaoxacyclooctadeca-2,11-diene,
2,3,8,9-dibenzo-1,4,7,10,13,16-hexaoxacyclooctadeca-2,8-diene,
2,3,11,12-dibenzo-1,4,7,10,13,16-hexaoxacyclooctadeca-2,11-diene,
2,3,11,12-bis(t-butylbenzo)-1,4,7,10,13,16-hexaoxacyclooctadeca-2,11-diene,
2,3,11,12-bis(2',3'-naphtho)-1,4,7,10,13,16-hexaoxacycloocta-2,11-diene,
2,3,12,13-dibenzo-1,4,11,14-tetraoxacycloeicosa-2,12-diene,
2,3,11,12-dibenzo-1,4,7,10,13,18-hexacyclodocosa-2,11-diene,
2,3,14,15-dibenzo-1,4,7,10,13,16,19,22-octaoxacyclotetracosa-2,14-diene,
2,3-benzo-1,4,7,10,13,16-hexaoxacyclooctadeca-2-ene,
2,3,8,9,14,15-tribenzo-1,4,7,10,13,16-hexaoxacyclooctadeca-2,8,14-triene,
2,3,9,10-dibenzo-1,4,8,11,14,17-hexaoxacyclononadeca-2,9-diene,
2,3,8,9,14,15-tribenzo-1,4,7,10,13,16-hexaoxacyclononadeca-2,8,14-triene,
2,3,11,12-dibenzo-1,4,7,10,13,16,19-heptaoxacycloheneicosa-2,11-diene,
2,3,8,9,14,15-tribenzo-1,4,7,10,13,16,19-heptaoxacyclohenicosa-2,8,14-triene,
2,3,8,9,14,15-tribenzo-1,4,7,10,13,16,19,22-octaoxacyclotetracosa-2,8,14-triene,
2,3,8,9,14,15,20,21-tetrabenzo-1,4,7,10,13,16,19,22-octaoxacyclotetracosa-2,8,14-triene,
2,3,15,16-dibenzo-1,4,9,14,17,22-hexaoxacyclohexacosa-2,15-diene,
2,3-(t-butylbenzo)-1,4,7,10,13,16-hexaoxacyclooctadeca-2-ene,
2,3-benzo-1,4,7,10-13-pentaoxacyclopentadeca-2-ene,
2,3-(t-butylbenzo)-1,4,7,10,13-pentaoxacyclopentadeca-2-ene, and
2,3,16,17-dibenzo-1,4,15,18-tetraoxacyclooctacosa-2,16-diene.

Other suitable macrocylic polyethers have the formulas

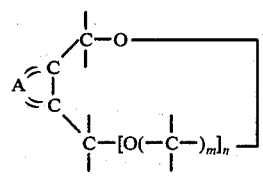

(IV)

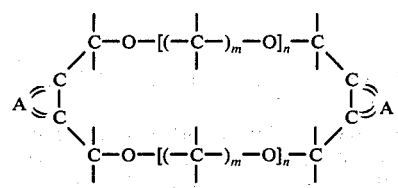

(V)

and

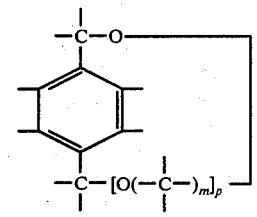

(VI)

in which formulas A and the two carbon atoms attached to A together represent a carbocyclic aromatic or hetero-aromatic group, m, n and p are integers from 2 to 10 inclusive, of at least 2 and of at least 3, respectively.

Examples of macrocyclic polyethers of formulas II, III, and IV include:
3,4-benzo-1,6,9,12,15,18,21-heptaoxacyclotricos-3-ene,
3,4-benzo-1,6,9,12-tetraoxacyclotetradec-3-ene,
3,4,17,18-dibenzo-1,6,9,12,15,20,23,26-octaoxacyclooctacos-3,17-diene,
3,4-benzo-1,6,9-trioxacycloundec-3-ene,
3,4-benzo-1,6,9,12,15-pentaoxacycloheptadec-3-ene,
3,4-benzo-1,6,9,12,15,18-hexaoxacycloeicos-3-ene,
3,4-1,6,9,12,15,18,21,24-octaoxacyclohexacos-3-ene,
3,4,14,15-dibenzo-1,6,9,12,17,20-hexaoxacyclodocos-3-ene,
3,4,17,18-dibenzo-1,6,9,12,15,20,23,26-octaoxacyclooctacos-3,17-diene,
3,4,20,21-dibenzo-1,6,9,12,15,18,23,26,29,32-decaoxacyclotetratriacont-3,20-diene,

[3,4-c]furo-1,6,9,12,15,18,21,24-octaoxacyclohexacos-3-ene,
[3,4-c]furo-1,6,9,12-tetraoxacyclotetradecane,
[3,4-c]furo-1,6,9,12,15-pentaoxacycloheptadecane,
[3,4-c]furo-1,6,9,12,15,18-hexaoxacycloeicosane,
[3,4-c]furo-1,6,9,12,15,18,21-heptaoxacyclotricosane,
[3,4-c]furo-1,6,9,12,15,18,21,24-octaoxacyclohexacosane,
3,4,14,15-difuro-1,6,9,12,17,,20-hexaoxacyclodocosane,
3,4,17,18-difuro-1,6,9,12,15,20,23,26-oxtaoxacyclooctacosane,
3,4,20,21-difuro-1,6,9,12,15,18,23,26,29,32-decaoxacyclotetratriacontane,
[3,4-c]furo-1,6,9,12-tetraoxacyclotetradec-3-ene,
[3,4-c] [17,18-c]difuro-1,6,9,12,15,20,23,26-octaoxacyclooctacos-3,17-diene,
[3,4-c]-2¹,5¹-dimethylthieno-1,6,9,12,15,18-hexaoxacycloeicos-3-ene,
3,4-(4¹, 5¹-methylene-dioxybenzo)-1,6,9,12,15,18,21-heptaoxacyclotricos-3-ene,
3,6-benzo-1,8,11,14-tetraoxacyclohexadec-3,5-diene,
3,6-benzo-1,8,11,14,17,pentaoxacyclononadec-3,5-diene,
3,6-benzo-1,8,11,14,17,20-hexaoxacyclodocosa-3,5-diene,
3,6-benzo-1,8,11,14,17,20,23-heptaoxacyclopentacosa-3,5-diene,
3,6-benzo-1,8,11,14,17,20,23,26-octaoxacyclooctacosa-3,5-diene,
and
3,6-benzo-1,8,11,14,17,20,23,26,29-nonaoxacyclohentriaconta-3,5-diene.

Other suitable catalysts are surface-active agents. A "surface-active agent" is defined as in Kirk-Othmer, "Encyclopedia of Chemical Technology", second edition, volume 19(1969), page 508: "An organic compound that encompasses in the same molecule two dissimilar structural groups, one being water-soluble and one being water-insoluble".

The surface-active agent is preferably non-ionic. Non-ionic synthetic surface-active agents may be broadly defined as compounds alphatic or alkylaromatic in nature which do not ionize in water solution. For example, a well known class of non-ionic agents is made available on the market under the trade name of "Pluronic." These compounds are formed by condensing ethylene oxide with an hydrophobic base formed by the condensation of propylene oxide with propylene glycol. The hydrophobic portion of the molecule which, of course, exhibits water insolubility has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product.

Other suitable nonionic agents include:

(1) The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octene, or nonene, for example.

(2) Those derived from the condensation of ethylene oxide with the product resulting from the reaction of propylene oxide and ethylenediamine. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said hydrophobic base having a molecular weight of the order of 2,500 to 3,000, are satisfactory.

(3) The condensation product of aliphatic alcohols having from 8 to 18 carbon atoms, in either straight chain or branched chain configuration, with ethylene oxide, e.g., a coconut alcohol-ethylene oxide condensate having from 10 to 30 moles of ethylene oxide per mole of coconut alcohol, the coconut alcohol fraction having from 10 to 14 carbon atoms.

(4) Long chain tertiary amine oxides corresponding to the following general formula, $R_1R_2R_3N \rightarrow O$, wherein $R_1$ is an alkyl radical of from about 8 to 18 carbon atoms, and $R_2$ and $R_3$ are each methyl or ethyl radicals. The arrow in the formula is a conventional representation of a semi-polar bond. Examples of amine oxides suitable for use in this invention include dimethyldodecylamine oxide, dimethyloctylamine oxide, dimethyldecylamine oxide, dimethyltetradecylamine oxide, dimethylhexadecylamine oxide.

(5) Long chain tertiary phosphine oxides corresponding to the following formula $RR'R''P \rightarrow O$, wherein R is an alkyl, alkenyl or monohydroxyalkyl radical ranging from 10 to 18 carbon atoms in chain length and R' and R" are each alkyl or monohydroxyalkyl groups containing from 1 to 3 carbon atoms. The arrow in the formula is a conventional representation of a semi-polar bond. Examples of suitable phosphine oxides are:
dimethyldodecylphosphine oxide,
dimethyltetradecylphosphine oxide,
ethylmethyltetradecylphosphine oxide,
cetyldimethylphosphine oxide,
dimethylstearylphosphine oxide,
cetylethylpropylphosphine oxide,
diethyldodecylphosphine oxide,
diethyltetradecylphosphine oxide,
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide.

(6) Dialkyl sulfoxides corresponding to the following formula, $RR'S \rightarrow O$, wherein R is an alkyl, alkenyl, beta- or gamma-monohydroxyalkyl radical or an alkyl or beta- or gamma-monohydroxyalkyl radical containing one or two other oxygen atoms in the chain, the R groups ranging from 10 to 18 carbon atoms in chain length, and wherein R' is methyl or ethyl. Examples of suitable sulfoxide compounds are:
dodecylmethyl sulfoxide
tetradecylmethyl sulfoxide
3-hydroxytridecylmethyl sulfoxide
2-hydroxydodecylmethyl sulfoxide
3-hydroxy-4-decoxybutylmethyl sulfoxide
3-hydroxy-4-dodecoxybutylmethyl sulfoxide
2-hydroxy-3-decoxypropylmethyl sulfoxide
2-hydroxy-3-dodecoxypropylmethyl sulfoxide
dodecylethyl sulfoxide
2-hydroxydodecylethyl sulfoxide (7) The ammonia, monoethanol and diethanol amides of fatty acids having an acyl moiety of from about 8 to about 18 carbon atoms;

(8) A sorbitan monoester with a long chain fatty acid of 8 to 20 carbon atoms; or (9) An alkylbenzene containing a straight-chain alkyl group. Suitable alkylbenzenes contain an alkyl group of 8 to 20 carbon atoms.

Preferred surface-active agents are poly(alkyleneoxy) derivatives formed by reacting a higher alcohol, alkylphenol or fatty acid with ethylene oxide or propylene oxide. Suitable alcohols, alkylphenols or fatty acids contain an alkyl group of from 8 to 20 carbon atoms and the number of alkyleneoxy units is in the range of 1 to 50. It is preferable to use an alcohol ethoxylate such as the ethoxylates derived by ethoxylation of primary or secondary, straight-chain or branched alcohols. A single alcohol may be used e.g., octyl alcohol, decyl alcohol, dodecyl alcohol, but preferably a mixture of alcohols is used. The mixture of alcohols may contain small amounts of alcohols below $C_7$ and above $C_{13}$ but at least 90%w, and preferably at least 95%w, of the alcohols thereof are in the $C_9$ to $C_{13}$ range. Preferred mixtures of alcohols are those mixtures of $C_9$ to $C_{11}$ alcohols such as those prepared by hydroformylation of olefins. The amount of ethylene oxide used to prepare such ethoxylates is suitably such so as to provide an average from 1 to 13 moles, and preferably 5 to 9 moles, of ethylene oxide per mole of alcohol (or alcohol mixture). Examples of such ethoxylates are "Dobanol$_{45-11}$" formed from a $C_{14}$ to $C_{15}$ straight-chain alcohol mixture and containing an average of eleven ethyleneoxy units or preferably "Dobanol$_{91-6}$" formed from a $C_9$ to $C_{11}$ straight-chain alcohol mixture with an average of six ethyleneoxy units (both trade names are registered trade marks).

The molar ratio of the amount of phase transfer catalyst to the amount of aromatic aldehyde of the formula ArC(O)H may vary within wide limits, but is suitably from 1:5 to 1:500. The use of low molar ratios will require a longer time to complete the reaction, whilst the use of higher molar ratios naturally increases the cost to produce a given quantity of ester. Thus, the choice of reaction time and molar ratio catalyst to aromatic aldehyde are mutually interdependant, and in any individual instance will depend on the local economic factors. Very good results are usually obtained at molar ratios from 1:10 to 1:100.

Another advantage of the process according to the present invention is that the molar ratio of the amount of (cyclo)aliphatic acyl halide to the amount of aromatic aldehyde can be kept so low that a molar excess of the halide is not or hardly not required. This molar ratio is preferably in the range of from 1.1 to 1.0. When the susbstantially water-immiscible aprotic solvent is a (cyclo)alkane or a mixture of (cyclo)alkanes molar ratios equal to 1.0 given excellent results.

The molar ratio of the amount of water-soluble cyanide to the amount of aromatic aldehyde is suitably from 1.5 to 1.00 and preferably from 1.3 to 1.02. By "water-soluble cyanide" is meant a water-soluble salt of hydrogen cyanide. Of the water-soluble cyanides alkali-metal cyanides and alkaline-earth-metal cyanides are preferred. Sodium cyanide is particularly preferred, because it affords the esters of the formula I in the shortest reaction time.

The optionally substituted aromatic group Ar in the aromatic aldehyde of the formula ArC(O)H may be carbocyclic or heterocyclic. Examples of carbocyclic groups are phenyl, 1-naphthyl, 2-naphthyl and 2-anthryl groups. Heterocyclic aromatic groups are derived from hetero-aromatic compounds which are defined as in Kirk-Othmer, "Encyclopedia of Chemical Technology", Second Edition, Volume 2(1963), page 702: obtained by replacement of one or more carbon atoms of a carbocyclic aromatic compound by a heteroatom — for example pyridine, pyrimidine, pyrazine, quinoline and isoquinoline — and also include those heterocyclic compounds having five-membered rings which show aromatic characteristics and are mentioned on page 703 of said volume, for example thiophene, pyrrole, furan, indole and benzothiophene. As an aromatic group an optionally substituted phenyl group is very suitable. Examples of substituents are hydrocarbyl and hydrocarbyloxy groups. Very good results have been obtained with phenoxybenzaldehydes such as m-phenoxybenzaldehyde.

The group R in the formula RC(O)Hal may, for example, be an optionally substituted alkyl group. The alkyl group may be straight or branched. The alkyl groups preferably have a tertiary or quaternary carbon atom bound to the group—C(O)Hal. Examples of such alkanoyl halides are 2-methylpropanoyl chloride, 2,2-dimethylpropanoyl chloride and 2-methylbutanoyl bromide. Very good results have been obtained with 2-methylpropanoyl chloride. The alkyl group may carry as substituents, for example, hydrocarbyloxy or sub-stititued phenyl groups, such as halophenyl or alkylphenyl. Very good results have been obtained with 1-(4-chlorophenyl)-2-methylpropyl groups. The expression "saturated cyclic hydrocarbyl group" in this patent application refers to cyclic hydrocarbyl groups in which the ring is saturated; this ring may carry substituents for example, alkyl groups of 1 to 6 carbon atoms, such as methyl, halogen atoms having atomic numbers of 9 to 35, inclusive, such as chlorine, bromine or fluorine, or unsaturated side chains such as isobutenyl, dichlorovinyl or dibromovinyl. Examples of saturated cyclic hydrocarbyl groups are cyclopropyl, cyclobutyl and cyclohexyl groups. Very goods results have been obtained with optionally substituted cyclopropanecarbonyl halides, particularly with 2,2,3,3-tetramethylcyclopropanecarbonyl halides and 2-(2,2-dichlorovinyl)-3,3-dimethylcyclopropanecarbonyl halides. The latter halide may have a cis or trans structure or may be a mixture of such structures and may be a pure optical isomer or a mixture of optical isomers.

The atom Hal in the formula RC(O)Hal preferably represents a chlorine or a bromine atom and in particular a chlorine atom.

The process according to the invention may be carried out by gradual addition of the acyl halide to a vigorously agitated, e.g, stirred, mixture of the other starting compounds (particularly recommended when R in the formula RC(O)Hal represents a 2,2,3,3-tetramethylcyclopropyl group) and often by placing together the total amounts of the starting compounds and vigorous agitating, e.g. stirring, of the mixture thus formed, which is particularly recommended when R represents a 1-(4-chlorophenyl)-2-methylpropyl, an isopropyl or a 2-(2,2-dichlorovinyl)-3,3-dimethylcyclopropyl group.

The process is of particular interest to prepare pesticidally active esters, for example: when the aromatic aldehyde is 3-phenoxybenzaldehyde and the acyl halide is an aralkyl halide such as 2-(4-chlorophenyl)-3-methylbutanoyl chloride or a substituted-cyclopropanecarbonyl halide such as 2,2,3,3-tetramethylcyclopropanecarbonyl chloride or 2-(2,2-dichlorovinyl)-3,3-dimethylcyclopropanecarbonyl chloride, because the esters then formed are α-cyano-3-phenoxybenzyl 2-(4-chlorophenyl)-3-methylbutanoate, α-cyano-3-phenoxybenzyl 2,2,3,3-tetramethylcyclopropanecarboxylate and α-cyano-3-phenoxybenzl 2-(2,2-dichlorovinyl)-3,3-dimethylcyclopropanecarboxylate, respectively, all of which are pesticidally active compounds as disclosed in Belgian Pat. No. 801,946, U.S. Pat. No. 3,835,176 and Netherlands Pat. No. 7,307,130, respectively.

EXAMPLES

The Examples further illustrate the invention. All the experiments were conducted at a temperature of 23° C, unless otherwise stated. The sodium cyanide used consisted of particles having a largest dimension of 0.5 mm and contained 0.44% by weight of water. The starting molar ratio of water to sodium cyanide has been calculated taking into account the water present in the sodium cyanide and the water added, if any. For comparison it may be stated that the molar ratio of water to sodium cyanide in a saturated aqueous solution of sodium cyanide having a temperature of 23° C is 4:1. The reaction mixtures were stirred vigorously and analysed by gas-liquid chromatography to determine the yield of the ester formed. Reaction mixtures were filtered to remove precipitated sodium chloride and solid sodium cyanide, if any, and drying of solutions was carried out over anhydrous sodium sulphate. Flashing of the solvent took place in a film evaporator at a pressure of 15 mm Hg. All yields are calculated on starting aromatic aldehyde.

EXAMPLE I

Preparation of α-cyano-3-phenoxybenzyl 2-(4-chlorophenyl)-3-methylbutanoate the presence of n-heptane A 50 ml round-bottomed flask equipped with a magnetic stirrer was charged with 10 mmol of 3-phenoxybenzaldehyde, 10 mmol of 2-(4-chlorophenyl)-3-methylbutanoyl chloride, 12 mmol of sodium cyanide, water, if any and 20 ml of n-heptane. The mixture thus formed was stirred and analysed.

Table I

| 1 | 2 | 3 | 4 | 5 | 6 |
|---|---|---|---|---|---|
| Ex. No. | Water added ml | Molar ratio water to NaCN | Special Conditions | Reaction time, h | Yield of ester, % |
| 1 | — | 0.001** | NaCN containing 0.04 %w of water was used | 20 | 87 |
| 2 | — | 0.012** | — | 2 | 91 |
|   |   |   |   | 18 | 100 |
| 3 | 0.02 | 0.105** | — | 0.5 | 89 |
|   |   |   |   | 1.0 | 100 |
| 4* | 1.00 | 4.64 | — | 3 | 86 |
|   |   |   |   | 18 more | than 99 |
| 5 | 0.02 | 0.120** | 0.0105 mol of NaCN was used | 1 | 94 |
|   |   |   |   | 3 more | than 99 |

*not according to the invention.
**solid NaCN is present.

Five experiments were conducted in the manner described above, see Table I. Column 1 states the number of the experiment, column 2 the amount of water added to the starting mixture, column 3 the molar ratio of water to sodium cyanide, column 4 conditions different from those described above and column 5 the reaction time. The yield of the ester wanted is presented in column 6.

The ester separated as a pale yellow oil during the reaction but dissolved on warming to a temperature between 40° and 50° C. The warm reaction mixture obtained in experiment 2 was filtered and the n-heptane was flashed from the filtrate to give the ester in quantitative yield as a pale yellow oil.

The reaction mixture obtained in experiment 3 was warmed to a temperature of 40-45° C and filtered. The n-heptane was flashed from the filtrate to obtain the ester in quantitative yield as a pale yellow oil with a purity of 98%.

EXAMPLE II

Preparation of five esters in the presence of n-heptane

A 50 ml round-bottomed flask equipped with a magnetic stirrer was charged with 10 mmol of an aromatic aldehyde, 10 mmol of a (cyclo)aliphatic acyl chloride, 12 mmol of sodium cyanide, 0.02 ml of water and 20 ml of n-heptane. The molar ratio of water to sodium cyanide was 0.105, solid NaCN being present. The mixture thus formed was stirred and analysed.

Five experiments were conducted in this manner, see Table II, experiments 1-5. Column 1 states the number of the experiment, column 2 the aromatic aldehyde used, column 3 the (cyclo)aliphatic acyl chloride used, column 4 the reaction time, column 5 the name of the ester formed and column 6 the yield of this ester.

Table II

| 1 | 2 | 3 | 4 | 5 | 6 |
|---|---|---|---|---|---|
| Exp. No. | Aromatic aldehyde | (Cyclo)aliphatic acyl chloride | Reaction time h | Name of the ester formed | Yield of the ester % |
| 1 | benzaldehyde | acetyl chloride | 3 | α-cyanobenzyl acetate | 14 |
|   |   |   | 22 |   | 38 |
| 2 | " | 2-methylpropanoyl chloride | 1 | α-cyanobenzyl isobutyrate | 96 |
|   |   |   | 2 |   | 99 |
| 3 | " | 2-(4-chlorophenyl)-3-methylbutanoyl | 1 | α-cyanobenzyl 2-(4-chlorophenyl)-3-methylbutanoate | 97 |
|   |   |   | 2 |   | 100 |
| 4 | " | 2,2,3,3-tetramethylcyclopropanecarbonyl chloride | 2 | α-cyanobenzyl 2,2,3,3-tetramethylcyclopropanecarboxylate | 52 |
|   |   |   | 5 |   | 81 |
|   |   |   | 21 |   | 91 |

Table II-continued

| Exp. No. | Aromatic aldehyde | (Cyclo)aliphatic acyl chloride | Reaction time h | Name of the ester formed | Yield of the ester % |
|---|---|---|---|---|---|
| 5 | 3-phenoxy-benzaldehyde | 2-(2,2-dichloro-vinyl)-3,3-dimethylcyclopropane-carbonyl chloride | 1 | α-cyano-3-phenoxybenzyl 2-(2,2-dichlorovinyl)-3,3-dimethyl-cyclopropanecarboxylate | 43 |
| 6* | " | " | 18 | " | 100 |
|  |  |  | 3 |  | 49 |
|  |  |  | 21 |  | 94 |
|  |  |  | 44 |  | 99 |

*not according to the invention.

The reaction mixture obtained in experiment 5 was warmed to a temperature between 40° and 45° C to dissolve the pale yellow oil that had separated, and filtered. The n-heptane was flashed from the filtrate to obtain the ester in quantitative yield.

Experiment 6 was a repetition of experiment 5, the difference being that 1.00 ml of water was added, the sodium cyanide being completely dissolved in the aqueous phase and the molar ratio of water to sodium cyanide being 4.64, and that 10.2 mmol of the acyl chloride was used.

EXAMPLE III

Preparation of α-cyano-3-phenoxybenzyl 2-(4-chlorophenyl)-3-methylbutanoate in the presence of toluene A 50 ml round-bottomed flask equipped with a magnetic stirrer was charged with 10 mmol of 3-phenoxybenzaldehyde, 10.5 mmol of 2-(4-chlorophenyl)-3-methylbutanoyl chloride, 12 mmol of sodium cyanide, 20 ml of toluene, a phase transfer catalyst, if any, and water, if any. The mixture thus formed was stirred and analysed. Ten experiments were conducted in this manner, see Table III, stating which catalysts and how much water was added, if any. The catalysts were applied in an amount of 0.20 mmol in the experiments 4 to 9 and of 1.0 mmol in experiment 10. Table III also presents the yield of the desired ester.

Table III

| Exp. No. | Catalyst | Water added ml | Molar ratio water to NaCn | Reaction time, h | Yield of ester, % |
|---|---|---|---|---|---|
| 1 | none | —[3] | 0.012 | 3 | 19 |
|  |  |  |  | 20 | 18 |
| 2 | none | 0.02[3] | 0.105 | 3 | 38 |
|  |  |  |  | 24 | 98 |
|  |  |  |  | 44 | 99 |
| 3[1] | none | 1.00 | 4.64 | 3 | 41 |
|  |  |  |  | 24 | 87 |
|  |  |  |  | 85 | 95 |
| 4 | 1,4,7,10,13,16-hexaoxacyclooctadecane | —[3] | 0.012 | 2 | 60 |
|  |  |  |  | 20 | 91 |
|  |  |  |  | 80 | 97 |
| 5 | " | 0.02[3] | 0.105 | 3 | 100 |
| 6[1] | " | 1.00 | 4.64 | 2 | 95 |
|  |  |  |  | 4 | 98 |
|  |  |  |  | 20 | 100 |
| 7 | tetra-n-butyl-ammonium bromide | —[3] | 0.012 | 2 | 30 |
|  |  |  |  | 22 | 32 |
| 8 | " | 0.02[3] | 0.105 | 2 | 81 |
|  |  |  |  | 18 | 98 |
| 9[1] | " | 1.00 | 4.64 | 2 | 71 |
|  |  |  |  | 22 | 81 |
|  |  |  |  | 44 | 86 |
| 10 | Dobanol 91-6[2] | 0.02[3] | 0.105 | 1 | 82 |

Table III-continued

| Exp. No. | Catalyst | Water added ml | Molar ratio water to NaCn | Reaction time, h | Yield of ester, % |
|---|---|---|---|---|---|
|  |  |  |  | 4 | 99 |

[1]not according to the invention.
[2]a registered trade name for a non-ionic surface-active agent formed from a $C_9$-$C_{11}$ alcohol mixture and containing an average of 6 ethyleneoxy units; the alcohol mixture consists of 85% n-alkanols and 15% 2-alkylalkanols.
[3]solid NaCN was present.

The reaction mixture obtained in experiment 5 was filtered (an oil had not separated) and the toluene was flashed from the filtrate to give the ester in quantitative yield, as a pale yellow oil. The purity of the ester was 98%.

EXAMPLE IV

Preparation of α-cyano-3-phenoxybenzyl 2-(4-chlorophenyl)-3-methylbutanoate in the presence of various solvents A 50 ml round-bottomed flask equipped with a magnetic stirrer was charged with 10 mmol of 3-phenoxybenzaldehyde, 10.0 or 10.5 mmol of 2-(4-chlorophenyl)-3-methylbutanoyl chloride, 12 mmol of sodium cyanide, 0.02 ml of water and 20 ml of an aprotic solvent. The molar ratio of water to sodium cyanide was 0.105, solid NaCN being present. Thirteen experiments were conducted in this manner, see Table IV, stating which solvents were used. Experiments 1, 2, 3, 4, 8 and 9 were conducted with 10.0 and the other experiments with 10.5 mmol of 2-(4-chlorophenyl)-3-methylbutanoyl chloride. The petroleum ether used in experiment 3 consisted of 97% by weight of alkanes and 3% by weight of benzene and had a boiling range at atmospheric pressure between 62° and 82° C. The ester remained in solution during the reaction in experiments 3 and 4. The reaction mixture obtained in experiment 4 was filtered and the cyclohexane was flashed from the filtrate to give the ester wanted as a colorless oil in quantitative yield. Table IV also presents the yields of the desired ester. Comparison of the yields shows that alkanes and cycloalkanes are the best solvents.

Table IV

| Experiment No. | Solvent | Reaction time, h | Yield of ester, % |
|---|---|---|---|
| 1 | n-heptane | 1.0 | more than 99 |
| 2 | 2,4,4-trimethylpentane | 1 | 92 |
|  |  | 2 | 99 |
| 3 | petroleum ether | 1 | 91 |
|  |  | 2 | 99 |
| 4 | cyclohexane | 1 | 80 |
|  |  | 3 | more than 99 |
| 5 | toluene | 3 | 38 |
|  |  | 24 | 98 |
| 6 | dichloromethane | 2 | 34 |

Table IV-continued

| Experiment No. | Solvent | Reaction time, h | Yield of ester, % |
|---|---|---|---|
| | | 18 | 46 |
| 7 | o-dichlorobenzene | 2 | 59 |
| | | 18 | 72 |
| 8 | diethyl ether | 3 | 54 |
| | | 20 | 91 |
| 9 | diisobutyl ketone | 20 | 80 |
| 10* | nitromethane | 5 | 5 |
| | | 21 | 13 |
| 11* | 1,4-dioxane | 18 | 0 |
| 12* | N,N-dimethylformamide | 5 | 5 |
| | | 21 | 7 |
| 13* | dimethylsulphoxide | 2 | 1 |
| | | 18 | 0 |

*not according to the invention, this solvent being water-miscible.

EXAMPLE V

Preparation of α-cyano-3-phenoxybenzyl 2-(4-chlorophenyl)-3-methylbutanoate in the presence of dichloromethane A 50 ml round-bottomed flask equipped with a magnetic stirrer was charged with 10 mmol of 3-phenoxybenzaldehyde, 10.5 mmol of 2-(4-chlorophenyl)-3-methylbutanoyl chloride, 12 mmol of sodium cyanide, 20 ml of dichloromethane, water, if any, and 0.20 mmol of tetra-n-butylammonium bromide. The mixture thus formed was stirred and analysed. Three experiments were conducted in this manner, each with a different amount of water. Table V states the amounts of water added and presents the yield of the desired ester.

Table V

| Exp. no. | Water added ml | Molar ratio of water to NaCN | Reaction time, h | Yield of ester, % |
|---|---|---|---|---|
| 1 | — | 0.012[2)] | 2 | 13 |
| | | | 22 | 13 |
| 2 | 0.02 | 0.105[2)] | 2 | 54 |
| | | | 18 | 84 |
| | | | 40 | 96 |
| 3[1)] | 1.00 | 4.64 | 3 | 65 |
| | | | 6 | 74 |
| | | | 70 | 87 |

[1)]not according to the invention.
[2)]solid NaCN was present.

EXAMPLE VI

Preparation of α-cyano-3-phenoxybenzyl 2-(4-chlorophenyl)-3-methylbutanoate in the presence of n-heptane on an enlarged scale A 500 ml round-bottomed flask equipped with a paddle stirrer was charged with 100 mmol of 3-phenoxybenzaldehyde, 100 mmol of 2-(4-chlorophenyl)-3-methylbutanoyl chloride, 120 mmol of sodium cyanide, 0.2 ml of water and 200 ml of n-heptane, the molar ratio of water to sodium cyanide being 0.105. The mixture was stirred (500 revolutions per minute) for 4 hours, after which time it was warmed to a temperature between 40° and 50° C and filtered. The n-heptane was flashed from the filtrate to leave the desired ester in quantitative yield and a purity of 97%.

What is claimed is:

1. A process for the preparation of an ester of the formula I

wherein Ar represents a phenoxy substituted phenyl group and R represents a branched-chain alkyl group substituted by a halophenyl group, which process comprises contacting an aromatic aldehyde of the formula ArC(O)H and an acyl halide of the formula RC(O)Hal, in which formulas Ar and R have the same meaning as in the formula I and Hal represents a halogen atom, in the presence of a substantially water-immiscible aprotic solvent comprising an alkane or cycloalkane containing 6 to 10 carbon atoms or a mixture thereof, with water and solid water-soluble cyanide in which the molar ratio of the amount of water to the total amount of water-soluble cyanide is in the range of 0.05 to 1 and recovering the desired ester product from the reaction mixture.

2. A process according to claim 1 in which the alkane is n-heptane.

3. A process according to claim 1, in which the cycloalkane is cyclohexane.

4. A process according to claim 1, in which the molar ratio of the amount of acyl halide of the formula RC(O)Hal to the amount of the aromatic aldehyde of the formula ArC(O)H is in the range of from 1.1 to 1.0.

5. A process according to claim 1, in which the molar ratio of the amount of acyl halide of the formula RC(O)Hal to the amount of the aromatic aldehyde of the formula ArC(O)H is 1.0.

6. A process according to claim 1, which is conducted at a temperature in the range of from 10° to 50° C.

7. A process according to claim 1, in which the water-soluble cyanide is sodium cyanide.

8. A process according to claim 1, in which Hal in the formula RC(O)Hal represents a chlorine atom.

9. A process according to claim 1, in which the group R in the formula RC(O)Hal is an optionally substituted alkyl group having a tertiary or quaternary carbon atom bound to the group —C(O)Hal.

10. A process according to claim 9, in which the group R is a 1-(4-chlorophenyl)-2-methylpropyl group.

11. A process according to claim 10, which is carried out by forming a mixture of the total amounts of the aromatic aldehyde, the acyl halide, the water, the water-soluble cyanide and the substantially water-immiscible aprotic solvent, and stirring of the mixture thus formed.

12. A process according to claim 1 conducted at a temperature of from 10° to 50° C wherein the aprotic solvent is n-heptane, 2,4,4-trimethylpentane, cyclohexane or petroleum ether and the cyanide is sodium cyanide.

13. A process according to claim 12 wherein the molar ratio of the amount of acyl halide of the formula RC(O)Hal to the amount of aromatic aldehyde of the formula ArC(O)H is in the range from 1.1 to 1.0.

14. A process according to claim 13 wherein the ester of formula I is α-cyano-3-phenoxybenzyl 2-(4-chlorophenyl)-3-methylbutanoate.

* * * * *